US012788778B2

(12) United States Patent
Konishi et al.

(10) Patent No.: US 12,788,778 B2
(45) Date of Patent: Nov. 10, 2026

(54) COMPOSITION FOR TREATING CENTRAL NERVOUS SYSTEM DISEASES, METHOD FOR PRODUCING COMPOSITION FOR TREATING CENTRAL NERVOUS SYSTEM DISEASES, AND METHOD FOR PRODUCING THERAPEUTIC FORMULATION FOR CENTRAL NERVOUS SYSTEM DISEASES

(71) Applicant: TWO CELLS CO., LTD., Hiroshima (JP)

(72) Inventors: Hiromu Konishi, Hiroshima (JP); Masaya Matsumoto, Hiroshima (JP); Kaori Iwamoto, Hiroshima (JP); Megumi Miyake, Hiroshima (JP); Koichiro Tsuji, Hiroshima (JP)

(73) Assignee: TWO CELLS CO., LTD., Hiroshima (JP)

( * ) Notice: Subject to any disclaimer, the term of this patent is extended or adjusted under 35 U.S.C. 154(b) by 457 days.

(21) Appl. No.: 18/011,367

(22) PCT Filed: Aug. 4, 2021

(86) PCT No.: PCT/JP2021/028948

§ 371 (c)(1),
(2) Date: Dec. 19, 2022

(87) PCT Pub. No.: WO2022/049977

PCT Pub. Date: Mar. 10, 2022

(65) Prior Publication Data

US 2023/0302055 A1 Sep. 28, 2023

(30) Foreign Application Priority Data

Sep. 3, 2020 (JP) ................................ 2020-148528

(51) Int. Cl.
*A61K 35/28* (2015.01)
*A61P 25/16* (2006.01)
*A61P 25/28* (2006.01)
*C12N 5/0775* (2010.01)

(52) U.S. Cl.
CPC .............. *A61K 35/28* (2013.01); *A61P 25/16* (2018.01); *A61P 25/28* (2018.01); *C12N 5/0668* (2013.01)

(58) Field of Classification Search
CPC ....... A61K 35/28; A61P 25/28; C12N 5/0668; C12N 2500/90
See application file for complete search history.

(56) References Cited

U.S. PATENT DOCUMENTS

| | | | | |
|---|---|---|---|---|
| 2006/0062771 | A1 | 3/2006 | Sasaki et al. | |
| 2006/0210544 | A1 | 9/2006 | Honmou et al. | |
| 2007/0178591 | A1 | 8/2007 | Honmou et al. | |
| 2008/0286246 | A1 | 11/2008 | Honmou et al. | |
| 2010/0254953 | A1 | 10/2010 | Honmou et al. | |
| 2010/0279412 | A1 | 11/2010 | Kato et al. | |
| 2011/0262393 | A1* | 10/2011 | Yang | A61P 25/02 435/375 |
| 2012/0201791 | A1* | 8/2012 | Yoo | A61P 29/00 424/93.7 |
| 2012/0329087 | A1 | 12/2012 | Tsuchiya et al. | |
| 2013/0195991 | A1 | 8/2013 | Ueda et al. | |
| 2015/0267172 | A1 | 9/2015 | Kato et al. | |
| 2016/0166734 | A1 | 6/2016 | Tsuji et al. | |
| 2016/0324898 | A1 | 11/2016 | Bolmont et al. | |
| 2017/0266234 | A1 | 9/2017 | Honmou | |
| 2018/0325946 | A1 | 11/2018 | Ueda et al. | |
| 2019/0255118 | A1 | 8/2019 | Honmou | |
| 2021/0128629 | A1 | 5/2021 | Kato et al. | |
| 2022/0031757 | A1 | 2/2022 | Kato et al. | |
| 2022/0112465 | A1 | 4/2022 | Lee | |

FOREIGN PATENT DOCUMENTS

| | | | |
|---|---|---|---|
| CN | 103037872 | A | 4/2013 |
| EP | 2194121 | A1 | 6/2010 |
| EP | 3117828 | A1 | 1/2017 |
| EP | 3563857 | A1 | 11/2019 |
| EP | 3865571 | A1 | 8/2021 |
| JP | 2012-157263 | | 8/2012 |
| WO | WO 2005-007176 | | 1/2005 |
| WO | WO 2007-080919 | | 7/2007 |
| WO | WO 2009-034708 | | 3/2009 |
| WO | WO 2011-111787 | | 9/2011 |

(Continued)

OTHER PUBLICATIONS

Boika et al. Mesenchymal stem cells in Parkinson's disease: Motor and nonmotor symptoms in the early posttransplant period. Surgical Neurology International • 2020 • 11(380), p. 1-8 (Year: 2020).*
Takamiya et al. Stem Cell Therapies for Intracerebral Hemorrhage: Review of Preclinical and Clinical Studies. Cell Transplantation vol. 32: 1-15 (Year: 2023).*
Li et al. Mesenchymal stem cells for regenerative medicine in central nervous system. Front Neurosci. Dec. 13, 2022;16 (Year: 2022).*
European search report for EP Patent Application No. 21864035.7, dated Jul. 12, 2024, 10 pages.
Li Ran et al: "TSG-6 attenuates inflammation-induced brain injury via modulation of microglial polarization in SAH rats through the SOCS3/STAT3 pathway", Journal of Neuroinflammation, vol. 15, No. 1,Aug. 20, 2018 (Aug. 20, 2018) 18 pages, XP093179464, GB ISSN: 1742-2094, DOI: 10.1186/s12974-018-1279-1.

(Continued)

*Primary Examiner* — Taeyoon Kim
(74) *Attorney, Agent, or Firm* — Casimir Jones, S.C.; Robert A. Goetz

(57) ABSTRACT

It is an object to provide a therapeutic composition for treatment of a central nervous disease, a method for producing a therapeutic composition for treatment of a central nervous disease, and a method for producing and preserving a therapeutic formulation for treatment of a central nervous disease. The object is attained by a therapeutic composition for treatment of a central nervous disease, containing synovial membrane-derived mesenchymal stem cells cultured in a serum-free medium.

4 Claims, 3 Drawing Sheets

(56) References Cited

FOREIGN PATENT DOCUMENTS

| | | | |
|---|---|---|---|
| WO | WO 2015-016357 | | 2/2015 |
| WO | WO 2018-123968 | | 7/2018 |
| WO | 2020/067774 | A1 | 4/2020 |

OTHER PUBLICATIONS

De Bari Cosimo et al: "Multipotent mesenchymal stem cells from adult human synovial membrane", Arthritis & Rheumatism, vol. 44, No. 8, Aug. 7, 2001 (Aug. 7, 2001) * pp. 1928-1942, XP093179299, US ISSN: 0004-3591, DOI: 10.1002/1529-0131(200108)44:8<1928::AID-AR T331>3.0.00;2-P * p. 1938, col. 2, par. 1 *.

International Preliminary Report on Patentability, International Patent Application No. PCT/JP2021/028948, dated Oct. 5, 2021, 9 total pages.

Kashafi et al., Transdifferentiation of human synovium-derived mesenchymal stem cell into neuronal-like cells in vitro. Journal of Jahrom University of Medical Sciences, 2013, vol. 11, No. 2, pp. 34-44.

Liu et al., Differentiation of temporomandibular joint synovial mesenchymal stem cells into neuronal cells in vitro: an in vitro study. Cell Biol Int. Jan. 2011;35(1):87-91.

Office Action for AU Patent Application No. 2021337035, dated Jan. 23, 2025, 4 pages.

Nishina, Hiroshi. et al., Development of a serum-free culture method for human skin stem cells . . . , Japanese Journal of Transplantation, 2010, vol. 45, No. 3, p. 301.

Shao, J. et al., Development of chemically defined serum-free media, The Chemical Times, Apr. 2020, vol. 2020, No. 2, pp. 17-22.

International Search Report for PCT/JP2021/028948 and its English translation, dated Oct. 5, 2021, 2 pages.

Cunningham, Catriona et al. "The therapeutic potential of the mesenchymal stem cell secretome in ischaemic stroke", Journal of Cerebral Blood Flow & Metabolism, 2018 vol. 38, No. 8, pp. 1276-1292.

Office Action for KR Patent Application No. 10-2023-7009736, dated Sep. 25, 2025, 5 pages.

Office Action for CN Patent Application No. 202180043870.5, dated May 23, 2026, 6 pages.

Office Action for EP Patent Application No. 21864035.7, dated Jul. 10, 2026, 10 pages.

Decision of Rejection for CN Patent Application No. 202180043870.5, dated Sep. 3, 2026, 6 pages.

* cited by examiner

COMPOSITION FOR TREATING CENTRAL NERVOUS SYSTEM DISEASES, METHOD FOR PRODUCING COMPOSITION FOR TREATING CENTRAL NERVOUS SYSTEM DISEASES, AND METHOD FOR PRODUCING THERAPEUTIC FORMULATION FOR CENTRAL NERVOUS SYSTEM DISEASES

TECHNICAL FIELD

The present invention relates to a therapeutic composition for treatment of a central nervous disease, a method for producing a therapeutic composition for treatment of a central nervous disease, a method for producing a therapeutic formulation for treatment of a central nervous disease, and a method for preserving a therapeutic formulation for treatment of a central nervous disease.

BACKGROUND ART

Diseases caused by an anomaly or injury in the central nervous system such as the brain or spinal cord (hereinafter also referred to as "central nervous diseases"), such as cerebral infarction, head injury, spinal cord injury, cerebrovascular dementia, Alzheimer's disease, and Parkinson's disease are treated by, for example, oral or injection administration, or surgical treatments. However, such treatments are symptomatic therapies, and a method for treating central nervous diseases has not been sufficiently established.

Mesenchymal stem cells (MSCs) can be isolated not only from tissues such as bone marrow, adipose, a synovial membrane, an alveolar bone, and a periodontal membrane, but also from various tissues such as a placenta, cord blood, and an umbilical cord. The mesenchymal stem cells can also be cultured and proliferated in vitro. Furthermore, the mesenchymal stem cells have multipotency that allows the mesenchymal stem cells to differentiate not only into mesenchymal cells (e.g., osteoblasts, adipose cells, and cartilage cells) but also into non-mesenchymal cells (e.g., neural precursor cells and hepatocytes). Thus, the mesenchymal stem cells are expected to be used as a material for production of cells for use in regenerative medicine or cell therapy.

A medium containing a serum such as a fetal bovine serum (FBS) is used to culture mesenchymal stem cells. This serum is used as a nutrient source for promoting in vitro growth or proliferation of cells or as a source of supply of a physiologically active substance such as hormone. However, in a case where cells are cultured in a serum-containing medium, there is a risk of contamination of the cultured cells by unknown pathogens (viruses, pathogenic prions, etc.) mixed in the serum. Examples of a method for avoiding the above problem include a method in which a serum-free medium containing no serum is used. For example, Patent Literatures 1 to 3 each disclose serum-free culture for use in culture of mesenchymal stem cells.

CITATION LIST

Patent Literatures

Patent Literature 1

International Publication No. WO 2007/080919

Patent Literature 2

International Publication No. WO 2011/111787

Patent Literature 3

International Publication No. WO 2015/016357

SUMMARY OF INVENTION

Technical Problem

Mesenchymal stem cells have a wide variety of functions, only part of which are currently being used. Thus, a new therapeutic approach to diseases such as a central nervous disease with use of mesenchymal stem cells is expected to be developed. However, it has been unclear what mesenchymal stem cells are suitable to treat central nervous diseases.

An aspect of the present invention is to provide, for example, a therapeutic composition for treatment of a central nervous disease, the therapeutic composition containing mesenchymal stem cells and being suitably used to treat the central nervous disease.

Solution to Problem

In the process of diligent study of an influence of mesenchymal stem cells on central nervous diseases, the inventors of the present invention found that synovial membrane-derived mesenchymal stem cells cultured in a serum-free medium have much higher effectiveness (e.g., an immunoregulation effect, an anti-inflammatory effect, a neovascular effect, and a neuroprotective effect) against central nervous diseases than mesenchymal stem cells cultured in a serum medium. The inventors of the present invention have thus completed the present invention.

Specifically, an embodiment of the present invention is arranged as below.

A therapeutic composition for treatment of a central nervous disease of an embodiment of the present invention contains synovial membrane-derived mesenchymal stem cells cultured in a serum-free medium.

A method for producing a therapeutic composition for treatment of a central nervous disease of an embodiment of the present invention includes the step of culturing synovial membrane-derived mesenchymal stem cells in a serum-free medium.

A method for producing a therapeutic formulation for treatment of a central nervous disease of an embodiment of the present invention includes: a cryopreservation step of suspending, in a cryopreservation solution, synovial membrane-derived mesenchymal stem cells cultured in a serum-free medium, and freezing a resulting suspension; and the step of melting the suspension and diluting the suspension so that the synovial membrane-derived mesenchymal stem cells have a concentration suitable for administration.

Note that mesenchymal stem cells contained in a therapeutic composition for treatment of a central nervous disease of an aspect of the present invention are specified by a production process such as a process of "being cultured in a serum-free medium". The inventors of the present invention carried out a test on presence or absence of genes (i.e., gene markers) which differ in expression level between mesenchymal stem cells for use in an aspect of the present invention and conventional mesenchymal stem cells (specifically, mesenchymal stem cells cultured in a serum medium). A result of the test made it clear that an enormous variety of genes differ in expression level, but was insufficient to specify which of these genes is important in distinguishing between mesenchymal stem cells for use in an aspect of the present invention and conventional mesenchymal stem cells. An enormous amount of time and effort is further necessary to specify what gene is important in distinguishing between mesenchymal stem cells for use in an aspect of the present invention and conventional mesenchymal stem cells. Thus, the inventors of the present invention concluded that there exist circumstances under which directly specifying mesenchymal stem cells of a therapeutic composition for treatment of a central nervous disease of an aspect of the present invention by its structure or properties at the time of filing the present application is impossible or impractical.

Advantageous Effects of Invention

It is possible to provide, for example, a therapeutic composition for treatment of a central nervous disease, the therapeutic composition containing mesenchymal stem cells and being suitably used to treat the central nervous disease.

DESCRIPTION OF EMBODIMENTS

Figure 1:
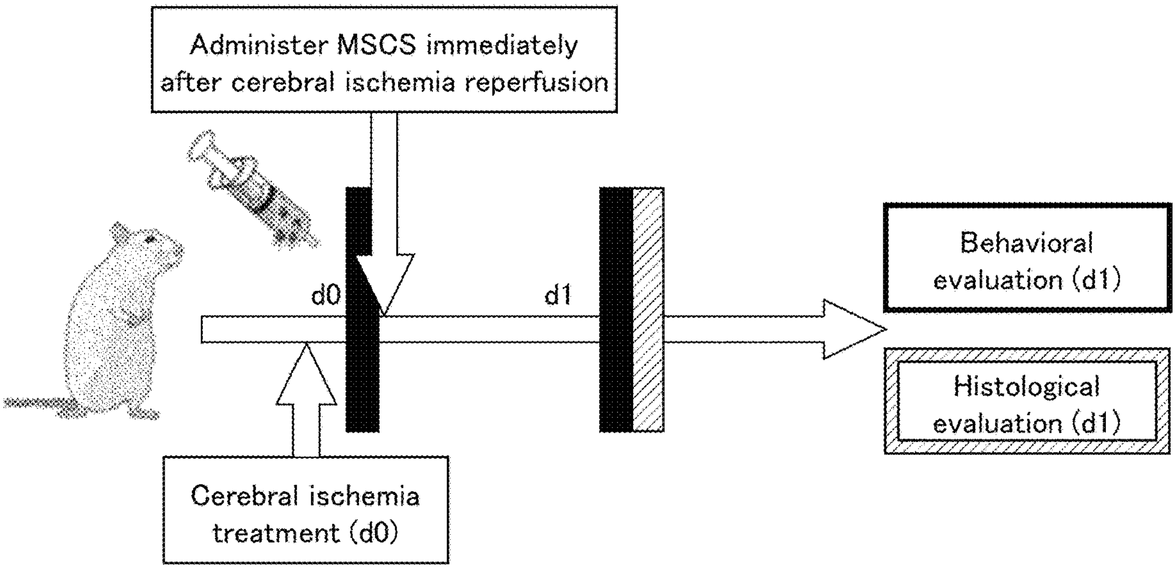
FIG. 1 is a diagram illustrating an outline of a procedure of an evaluation method in accordance with Example 1.

The following description will discuss an embodiment of the present invention. The present invention is not, however, limited to these embodiments. The present invention is not limited to the arrangements described below, but may be altered within the scope of the claims by a person skilled in the art. The present invention also encompasses, in its technical scope, any embodiment derived by combining technical means disclosed in differing embodiments and Examples. All academic and patent documents cited in the present specification are incorporated herein by reference. Any numerical range expressed as "A to B" in the present specification means "not less than A and not more than B (i.e., a range from A to B which includes both A and B)" unless otherwise stated.

The term "serum-free medium" is herein intended to mean a medium that contains no serum, and the term "serum-free culture" is herein intended to mean a culture in which no serum is used. Furthermore, the term "mesenchymal stem cell" herein means a stem cell derived from a cell belonging to the mesenchymal lineage. The mesenchymal stem cell also encompasses (i) a cell obtained by further isolating, from a mesenchymal stem cell, a cell having a specific property, (ii) a cell obtained by providing a mesenchymal stem cell with some stimulus such as a cytokine stimulus, and (iii) a cell obtained by introducing a gene into a mesenchymal stem cell. For example, the mesenchymal stem cell also encompasses, for example, a MUSE cell and a MAPC cell. The mesenchymal stem cell is preferably a human mesenchymal stem cell, but may also be a mesenchymal stem cell derived from a non-human mammal such as a rat or a mouse. A synovial membrane is roughly divided into (i) a fibrotic synovial membrane that covers an intracapsular femur or joint capsule and (ii) a fatty synovial membrane of an infrapatellar fat body. The term "synovial membrane-derived mesenchymal stem cell" is herein intended to mean both a fibrotic synovial membrane-derived mesenchymal stem cell and a fatty synovial membrane-derived mesenchymal stem cell.

The expression "therapeutic composition for treatment of a central nervous disease" is herein intended to mean a pharmaceutical agent that has an effect of promoting recovery and/or regeneration from a central nervous disease. The therapeutic composition for treatment of a central nervous disease includes not only a composition in which mesenchymal stem cells are used in their original state without any change in their function but also a composition in which cells are used that have enhanced functions such as secretion capability and differentiation potency by being cultured and proliferated under a specific condition.

[1. Method for Producing Therapeutic Composition for Treatment of Central Nervous Disease]

A method for producing a therapeutic composition for treatment of a central nervous disease in accordance with an embodiment of the present invention (hereinafter also referred to as a "production method of the present embodiment") is a method including the step of culturing synovial membrane-derived mesenchymal stem cells in a serum-free medium.

(1-1. Serum-Free Medium)

In the production method of the present embodiment, a makeup of the serum-free medium in which the synovial membrane-derived mesenchymal stem cells are cultured is not particularly limited. A makeup of a known serum-free medium can be used as appropriate. A basal medium for constituting the serum-free medium is not limited to any particular basal medium provided that the basal medium is a known medium for mammalian cells. Examples of a preferable basal medium include a Ham's F12 medium, a DMEM medium, an RPMI-1640 medium, and an MCDB medium. Those basal media each may be used alone, or a mixture of two or more of the basal media may be used. In an embodiment, a basal medium for constituting the serum-free medium is preferably a medium in which MCDB and DMEM are mixed at a ratio of 1:1.

In an embodiment, a serum-free medium may be alternatively used that is obtained by adding, to the basal medium, for example, a platelet-derived growth factor (PDGF), an epidermal growth factor (EGF), a transforming growth factor-β (TGF-β), a hepatocyte growth factor (HGF), at least one phospholipid, at least one fatty acid, and the like.

By using such a serum-free culture medium to culture mesenchymal stem cells, it is possible to (i) prevent contamination of cultured cells due to mixing of unknown pathogens (viruses, pathogenic prions, etc.) in the serum-free medium and (ii) obtain a proliferation promoting effect equal to or greater than that obtained in a case where a serum-containing medium is used.

A PDGF is contained at a final concentration of preferably 0.5 ng/mL to 100 ng/mL, and more preferably ng/mL, relative to the basal medium. An EGF is contained at a final concentration of preferably 0.5 ng/mL to 200 ng/mL, and more preferably 20 ng/mL, relative to the basal medium.

In a case where the basal medium contains a TGF-β, the TGF-β is contained at a final concentration of preferably 0.5 ng/mL to 100 ng/mL, and more preferably ng/mL, relative to the basal medium. In a case where the basal medium contains an HGF, the HGF is contained at a final concentration of preferably 0.1 ng/mL to 50 ng/mL, and more preferably 5 ng/mL, relative to the basal medium.

A total of phospholipid(s) is contained at a final concentration of preferably 0.1 μg/mL to 30 μg/mL, and more preferably 10 μg/mL, relative to the basal medium. A total amount of fatty acid(s) contained relative to the basal medium is preferably 1/1000 to 1/10, and more preferably 1/100 of a weight of the basal medium.

The phospholipid that is added to the basal medium is exemplified by, but not particularly limited to, phosphatidic acid, lysophosphatidic acid, phosphatidylinositol, phosphatidyl serine, phosphatidyl ethanolamine, phosphatidyl choline, and phosphatidyl glycerol. Those phospholipids each may be used alone, or two or more of the phospholipids may be used in combination (for example, phosphatidic acid and phosphatidyl choline may be used in combination). Those phospholipids may be derived from animals or plants.

The fatty acid that is added to the basal medium is exemplified by, but not particularly limited to, linoleic acid, oleic acid, linolenic acid, arachidonic acid, myristic acid, palmitoyl acid, palmitic acid, and stearic acid. Those fatty acids each may be used alone, or two or more of the fatty acids may be used in combination. Furthermore, the serum-free medium in accordance with the present embodiment may contain not only the fatty acid(s) but also cholesterol.

The PDGF is herein intended to mean a growth factor selected from a platelet derived growth factor (PDGF) family, and is preferably a PDGF-BB or a PDGF-AB. The EGF is herein intended to mean a growth factor selected from an epidermal growth factor (EGF) family.

The serum-free medium may further contain any of a connective tissue growth factor (CTGF), a vascular endothelial growth factor (VEGF), and an ascorbic acid compound.

The ascorbic acid compound is herein intended to mean ascorbic acid (vitamin C), ascorbate diphosphate, or a compound similar to ascorbic acid or ascorbate diphosphate.

The serum-free medium may contain a lipid antioxidant. Examples of the lipid antioxidant include DL-α-tocopherol acetate (vitamin E). Furthermore, the serum-free medium may further contain a surfactant. Examples of the surfactant include PLURONIC® (registered trademark) F-68 and TWEEN® (registered trademark) 80.

The serum-free medium may further contain insulin, transferrin, dexamethasone, serum albumin, and selenate. Herein, insulin may be an insulin-like growth factor, may be derived from a natural cell, or may be produced by genetic modification. Note that the serum-free medium which contains at least any one of dexamethasone, insulin, and serum albumin brings about an effect of (i) extending a lifetime of mesenchymal stem cells and (ii) accelerating proliferation of mesenchymal stem cells.

In the production method of the present embodiment, the serum-free medium may be a known serum-free medium. Examples of the known serum-free medium include STK® (registered trademark) 1 (manufactured by TWOCELLS COMPANY, LIMITED), STK® (registered trademark) 2 (manufactured by TWOCELLS COMPANY, LIMITED), a kit for a complete synthetic medium dedicated for human mesenchymal stem cells (MSCGM-CD BulletKit) (Lonza), a mesenchymal stem cell growth medium DXF (Ready-touse) (PromoCell GmbH.), Stem Pro MSC SFM Xeno Free (Thermo Fisher Scientific Inc.), and MesenCult-ACF Medium Kit (STEMCELL Technologies Inc.).

(1-2. Culture Condition)

In the production method of the present embodiment, synovial membrane-derived mesenchymal stem cells isolated from animal tissues or cells such as human tissues or cells by a conventionally known method are inoculated and cultured in the serum-free medium described earlier. Regarding a culture condition, for example, synovial membrane-derived mesenchymal stem cells separated from 1 mg to 500 mg of a tissue piece(s) (containing mesenchymal stem cells) are preferably inoculated per 1 mL of a medium at a culture temperature of 37° C.±1° C. and under 5% $CO_2$.

Note that a culture time is not limited to any particular culture time provided that the culture time allows a concentration of the synovial membrane-derived mesenchymal stem cells to reach an intended concentration. For example, the culture time may be 1 hour to 5 hours, 1 hour to 10 hours, 1 hour to 20 hours, hour to 1 day, 1 hour to 10 days, 1 hour to 30 days, hour to 50 days, 30 hours to 70 hours, 40 hours to 70 hours, or 50 hours to 70 hours. By thus culturing the synovial membrane-derived mesenchymal stem cells, it is possible to efficiently produce a large number of synovial membrane-derived mesenchymal stem cells the immunosuppression ability of which is maintained or improved.

The synovial membrane-derived mesenchymal stem cells that are used in the production method of the present embodiment are preferably exemplified by, but not particularly limited to, initial mesenchymal stem cells, i.e., cells which have never been subcultured since the cells were collected from animal tissues such as human tissues.

A culture vessel for use in culture is not limited to any particular culture vessel provided that the culture vessel allows the synovial membrane-derived mesenchymal stem cells to be proliferated. Preferable examples of the culture vessel include a 75 $cm^2$ flask (manufactured by Falcon) and a 75 $cm^2$ flask (manufactured by SUMITOMO BAKELITE CO., LTD.). Note, however, that proliferation of some cells may be affected by a type of culture vessel used. Thus, in order to more efficiently proliferate the mesenchymal stem cells, it is preferable to use a culture vessel suitable for proliferation to culture each of mesenchymal stem cells to be proliferated (hereinafter also referred to as "proliferation target cells").

Examples of a method for selecting the culture vessel suitable for proliferation include a method in which an optimum culture vessel is selected by the proliferation target cells. Specifically, a plurality of types of culture vessels are prepared, and proliferation target cells are proliferated under the same culture condition except that the culture vessels differ in type. After 2 weeks from the start of culture, the number of cells contained in each of the culture vessels is measured by a known method. Then, it can be determined that a culture vessel containing the largest number of cells is the most suitable for proliferation of the proliferation target cells. Furthermore, in a case where the proliferation target cells are proliferated at a high speed, it can be determined, even before 2 weeks have elapsed from the start of culture, that a culture vessel in which the number of proliferation target cells reaches 80% to 90% of the number of cells in a confluent state in the shortest period is the most suitable for proliferation of the proliferation target cells.

Note that adhesion of mesenchymal stem cells to a culture vessel is a requisite to proliferation of the mesenchymal stem cells. Thus, in a case where the proliferation target cells less strongly adhere to the culture vessel, the serum-free medium preferably further contains cell adhesion molecules during serum-free culture. Examples of the cell adhesion molecules include fibronectin, collagen, and gelatin. One type of those cell adhesion molecules may be used alone, or two or more types of the cell adhesion molecules may be used in combination.

The cell adhesion molecules are contained at a final concentration of more preferably 1 μg/mL to 50 μg/mL, and preferably 5 μg/mL, relative to the serum-free medium. In an embodiment, in a case where the cell adhesion molecules are fibronectin, the fibronectin is added so as to have a final concentration of 5 μg/mL relative to the serum-free medium. This enables the proliferation target cells to adhere to the culture vessel with higher efficiency.

In the serum-free culture, the mesenchymal stem cells may be subcultured at least once. The mesenchymal stem cells are anchorage-dependently proliferated. Thus, for example, in a case where the mesenchymal stem cells are locally unevenly proliferated, by subculturing the mesenchymal stem cells that are being proliferated, it is possible to culture the mesenchymal stem cells under a better condition.

The mesenchymal stem cells do not necessarily need to be subcultured by any particular method, but can be subcultured by a conventionally known method for subculturing mesenchymal stem cells. In a case where the mesenchymal stem cells are subcultured, a cell detaching agent containing neither a mammal-derived component nor a microorganism-derived component is preferably used to detach the mesenchymal stem cells so that subcultured mesenchymal stem cells will be in good condition. Examples of the "cell detaching agent containing neither a mammal-derived component nor a microorganism-derived component" include TrypLE Select (Life Technologies) and ACCUTASE (Innovative Cell Technologies, Inc.).

[2. Therapeutic Composition for Treatment of Central Nervous Disease]

A therapeutic composition for treatment of a central nervous disease in accordance with an embodiment of the present invention (hereinafter referred to as a "therapeutic composition of the present embodiment") contains synovial membrane-derived mesenchymal stem cells cultured in a serum-free medium.

The synovial membrane-derived mesenchymal stem cells contained in the therapeutic composition of the present embodiment are synovial membrane-derived mesenchymal stem cells described in [1. Method for producing therapeutic composition for treatment of central nervous disease] and cultured in a serum-free medium. That is, the mesenchymal stem cells contained in the therapeutic composition of the present embodiment are synovial membrane-derived mesenchymal stem cells proliferated in the method described earlier for producing a therapeutic composition for treatment of a central nervous disease.

The therapeutic composition of the present embodiment has an effect of promoting recovery and/or regeneration from a central nervous disease. It is known that mesenchymal stem cells differ in differentiation potency and expression of secretory factors depending on tissues derived from, for example, bone marrow, adipose, and an umbilical cord. The inventors of the present invention found that synovial membrane-derived mesenchymal stem cells cultured in a serum-free medium have a higher immunoregulation effect, a higher anti-inflammatory effect, a higher neovascular effect, and a higher neuroprotective effect than mesenchymal stem cells cultured in a serum-containing medium. It is therefore considered that an aspect of the present invention brings about a therapeutic effect to a central nervous disease which effect cannot be achieved in a case where mesenchymal stem cells cultured in a serum-containing medium are used and which effect is remarkably high (i.e., so high as to be available for a clinical site). Numerous studies have been conducted to treat a central nervous disease with use of mesenchymal stem cells. In such studies, mesenchymal stem cells of the central nervous system (e.g., bone marrow, etc.) have been ordinarily used. Note, however, that the inventors of the present invention have acquired new knowledge that a remarkable effect of promoting recovery and/or regeneration from a central nervous disease is brought about in a case where mesenchymal stem cells derived from a synovial membrane, which is a structure of a locomotorium and which has been considered to be less associated with the central nervous system, are cultured in a serum-free medium.

Furthermore, the therapeutic composition of the present embodiment contains serum-free cultured synovial membrane-derived mesenchymal stem cells. Thus, there is no risk of administration, into a patient body, of unknown pathogens (viruses, pathogenic prions, etc.) mixed in a serum. Moreover, a serum is very expensive. In addition, since components of a serum vary in each lot because the serum is a natural product, the serum tends to cause a variation in cell proliferation effect. However, the present invention, in which no serum is used, never causes such a problem. Further, it is unnecessary to purify cultured mesenchymal stem cells in order to remove therefrom serum-derived proteins, etc. This makes operations more efficient.

A central nervous disease for which the therapeutic composition of the present embodiment is effective is not particularly limited. Examples of such a central nervous disease include cerebral infarction, cerebral hemorrhage, head injury, spinal cord injury, Alzheimer's disease, cerebrovascular dementia, Parkinson's disease, Huntington's disease, multiple sclerosis, and amyotrophic lateral sclerosis.

The therapeutic composition of the present embodiment may be a pharmaceutical agent containing synovial membrane-derived mesenchymal stem cells cultured in a serum-free medium. The therapeutic composition of the present embodiment can contain not only mesenchymal stem cells cultured in a serum-free medium but also a pharmaceutically acceptable additive(s) (e.g., a buffer, an antioxidant, a thickener, and/or an excipient).

An amount of the additive(s) contained is not limited to any particular amount, but can be, for example, 0.01% by weight to 50% by weight, 0.01% by weight to 40% by weight, 0.01% by weight to 30% by weight, 0.01% by weight to 20% by weight, 0.01% by weight to 10% by weight, or 0.01% by weight to 1% by weight, of the therapeutic composition of the present embodiment.

The number of mesenchymal stem cells contained in the therapeutic composition of the present embodiment is not limited to any particular number and can be set as appropriate in accordance with a body weight of a target to which the therapeutic composition is to be administered. For example, $1\times10^2$ mesenchymal stem cells to $1\times10^{10}$ mesenchymal stem cells, $1\times10^3$ mesenchymal stem cells to $1\times10^{10}$ mesenchymal stem cells, $1\times10^4$ mesenchymal stem cells to $1\times10^{10}$ mesenchymal stem cells, $1\times10^5$ mesenchymal stem cells to $1\times10^{10}$ mesenchymal stem cells, or $1\times10^{6}$ mesenchymal stem cells to $1\times10^{10}$ mesenchymal stem cells can be contained per administration. It is a matter of course that $10^{10}$ or more mesenchymal stem cells may be contained per administration.

Examples of a method of administration of the therapeutic composition include an intravenous injection, an intraarterial injection, and local injections (e.g., an intraspinal injection (intracavity injection), an intramuscular injection, an intraarticular injection, an intraventricular injection, etc.). Among those methods of administration of the therapeutic composition, a method in which a catheter is used to administer the therapeutic composition to an artery at or near an affected part brings about an advantageous effect of achieving a smaller number of cells necessary for administration of the therapeutic composition.

A target to which the therapeutic composition of the present embodiment is to be administered is not particularly limited. For example, in a case where the therapeutic composition of the present embodiment contains human synovial membrane-derived mesenchymal stem cells, examples of the target to which the therapeutic composition is to be administered include a human and non-human mammals (cattle, a pig, a sheep, a goat, a horse, a dog, a cat, a rabbit, a mouse, a rat, etc.). In a case where the therapeutic composition of the present embodiment contains synovial membrane-derived mesenchymal stem cells of a non-human mammal, the therapeutic composition may be administered to the non-human mammal or the target that is not the non-human mammal, such as a human. That is, the mesenchymal stem cells of the therapeutic composition of the present embodiment may be transplanted into an animal of a different kind or may be transplanted into an animal of the same kind. Transplantation into an animal of the same kind may be autotransplantation or allotransplantation.

An amount of administration of the therapeutic composition of the present embodiment is not limited to any particular amount, but can be an amount that causes $1\times10^{2}$ mesenchymal stem cells to $1\times10^{9}$ mesenchymal stem cells, $1\times10^{3}$ mesenchymal stem cells to $1\times10^{9}$ mesenchymal stem cells, $1\times10^{4}$ mesenchymal stem cells to $1\times10^{9}$ mesenchymal stem cells, $1\times10^{5}$ mesenchymal stem cells to $1\times10^{9}$ mesenchymal stem cells, or $1\times10^{6}$ mesenchymal stem cells to $1\times10^{9}$ mesenchymal stem cells to be administered per kilogram of body weight of the target to which the therapeutic composition is to be administered.

[3. Method for Producing Therapeutic Formulation for Treatment of Central Nervous Disease]

A method for producing a therapeutic formulation for treatment of a central nervous disease in accordance with an embodiment of the present invention (method for producing a therapeutic formulation of the present embodiment) includes: a cryopreservation step of suspending, in a cryopreservation solution, synovial membrane-derived mesenchymal stem cells cultured in a serum-free medium, and freezing a resulting suspension; and the step of melting the suspension and diluting the suspension so that the synovial membrane-derived mesenchymal stem cells have a concentration suitable for administration.

The expression "therapeutic formulation for treatment of a central nervous disease" is herein intended to mean a formulation into which a pharmaceutical agent that has an effect of promoting recovery and/or regeneration from a central nervous disease has been prepared so as to be in a state suitable for administration. The therapeutic formulation for treatment of a central nervous disease includes not only a formulation into which mesenchymal stem cells in their original state without any change in their function have been prepared, but also a formulation into which cells that have enhanced functions such as differentiation potency by being cultured and proliferated under a specific condition have been prepared.

The synovial membrane-derived mesenchymal stem cells used in the method for producing a therapeutic formulation of the present embodiment are synovial membrane-derived mesenchymal stem cells described in [1. Method for producing therapeutic composition for treatment of central nervous disease] and cultured in a serum-free medium. That is, the mesenchymal stem cells used in the method for producing a therapeutic formulation of the present embodiment are synovial membrane-derived mesenchymal stem cells proliferated in the method described earlier for producing a therapeutic composition for treatment of a central nervous disease.

The method for producing a therapeutic formulation of the present embodiment includes a cryopreservation step of suspending, in a cryopreservation solution, synovial membrane-derived mesenchymal stem cells cultured in a serum-free medium, and freezing a resulting suspension.

In the method for producing a therapeutic formulation of the present embodiment, a makeup of a preservative solution for freezing the synovial membrane-derived mesenchymal stem cells described earlier is not particularly limited. The makeup may be a makeup of a known preservative solution as appropriate. For example, the preservative solution may contain, for example, an infusion solution, a cryoprotective agent, and/or albumin.

The infusion solution is exemplified by, but not limited to, Ringer's solution bicarbonate. The Ringer's solution bicarbonate may be a commercially available infusion and is suitably exemplified by BICARBON® (registered trademark) infusion (AY PHARMACEUTICALS CO., LTD.). One type of infusion solution may be used alone, or a plurality of types of infusion solutions may be used in combination.

The cryoprotective agent that prevents or reduces growth of ice crystals in cells during a freezing/thawing process is exemplified by, but not limited to, dimethyl sulfoxide (DMSO). An amount of the cryoprotective agent in the preservative solution in accordance with an embodiment of the present invention is more preferably 0.5% (v/v) to 50% (v/v) relative to a total amount of the preservative solution.

The preservative solution in accordance with an embodiment of the present invention may contain albumin in order to more suitably protect cells during the freezing/thawing process. In a case where albumin is added to the preservative solution, the albumin is contained at a concentration of more preferably 0.25% (v/v) to 25% (v/v) relative to the total amount of the preservative solution.

In the cryopreservation step, the synovial membrane-derived mesenchymal stem cells are suspended in the preservative solution described earlier. The mesenchymal stem cells are preferably suspended in the preservative solution by, for example, a method in which the preservative solution is put into a container that allows cryopreservation, and the mesenchymal stem cells are suspended in the preservative solution.

A ratio between an amount of the preservative solution and an amount of the mesenchymal stem cells in a case where the mesenchymal stem cells are suspended in the preservative solution is not particularly limited provided that the amount of the mesenchymal stem cells suspended in the preservative solution allows cryopreservation. The amount of those mesenchymal stem cells is, for example, approximately 500,000 cells/mL to 10,000,000 cells/mL. The amount of the mesenchymal stem cells relative to the preservative solution enables the mesenchymal stem cells to be sufficiently suspended in the preservative solution.

A suspension obtained by suspending the synovial membrane-derived mesenchymal stem cells in the preservative solution is frozen. A freezing temperature may be set as appropriate to a temperature at which the mesenchymal stem cells are frozen. The freezing temperature may be, for example, not more than −80° C. or not more than −196° C. In a case where the suspension is frozen at not more than −80° C., for example, a conventionally known example or the like may be used. In a case where the suspension is frozen at not more than −196° C., liquid nitrogen may be used.

Furthermore, the method for producing a therapeutic formulation of the present embodiment includes the step of melting the suspension described earlier and diluting the suspension so that the mesenchymal stem cells have a concentration suitable for administration.

In the method for producing a therapeutic formulation of the present embodiment, the suspension may be melted at a temperature that does not cause cell injury. The temperature is preferably not less than 10° C. and not more than 45° C., more preferably not less than 20° C. and not more than 40° C., and even more preferably not less than 35° C. and not more than 40° C. For example, a hot water bath at 35° C. to 38° C. is preferably used to melt the suspension. This is because such a method achieves rapid melting of the suspension, a higher cell recovery, and a higher cell survival rate.

The molten suspension is diluted with a diluent such as a physiological saline solution or Ringer's solution. The diluent is not particularly limited and may be any diluent that allows the synovial membrane-derived mesenchymal stem cells to maintain their function. A dilution concentration may be prepared so that the mesenchymal stem cells have a concentration suitable for administration. For example, the dilution concentration may be prepared so that the number of mesenchymal stem cells reaches appropriately 500,000 cells/mL to 3,000,000 cells/mL.

An embodiment of the present invention may be arranged as below.

<1> A therapeutic composition for treatment of a central nervous disease, containing synovial membrane-derived mesenchymal stem cells cultured in a serum-free medium.

<2> The therapeutic composition recited in <1>, wherein the central nervous disease is at least one selected from the group consisting of cerebral infarction, cerebral hemorrhage, head injury, and spinal cord injury.

<3> The therapeutic composition recited in <1>, wherein the central nervous disease is at least one selected from the group consisting of Alzheimer's disease, cerebrovascular dementia, Parkinson's disease, Huntington's disease, multiple sclerosis, and amyotrophic lateral sclerosis.

<4> A method for producing a therapeutic composition for treatment of a central nervous disease, including the step of culturing synovial membrane-derived mesenchymal stem cells in a serum-free medium.

<5> A method for producing a therapeutic formulation for treatment of a central nervous disease, including: a cryopreservation step of suspending, in a cryopreservation solution, synovial membrane-derived mesenchymal stem cells cultured in a serum-free medium, and freezing a resulting suspension; and the step of melting the suspension and diluting the suspension so that the synovial membrane-derived mesenchymal stem cells have a concentration suitable for administration.

EXAMPLES

Example 1

(Evaluation of Effectiveness of Synovial Membrane-Derived Mesenchymal Stem Cells Against Cerebral Infarction)

Example 1 carried out a study on an improvement in sequelae of cerebral infarction due to transplantation of synovial membrane-derived mesenchymal stem cells cultured in a serum-free medium.

FIG. 1 illustrates an outline of a procedure of an evaluation method in accordance with Example 1. As illustrated in FIG. 1, Example 1 produced a cerebrally infarcted model rat, administered mesenchymal stem cells (MSCs) to the cerebrally infarcted model rat immediately after cerebral ischemia reperfusion, and carried out behavioral evaluation and histological evaluation after the elapse of 1 day from the administration.

According to a well-known method (e.g., an explant method or a collagenase method), mesenchymal stem cells were separated and cultured from a human synovial membrane or bone marrow tissue in a serum-free medium STK® (registered trademark) 1 (TWOCELLS COMPANY, LIMITED) or a 10% bovine serum-containing DMEM medium (Sigma-Aldorich). Synovial membrane mesenchymal stem cells separated in the serum-free medium STK® (registered trademark) 1 were inoculated into a serum-free medium STK® (registered trademark) 2 (TWOCELLS COMPANY, LIMITED), and synovial membrane or bone marrow mesenchymal stem cells separated in the 10% bovine serum-containing DMEM medium were inoculated into the serum-free medium STK® (registered trademark) 2. The synovial membrane mesenchymal stem cells separated in the serum-free medium STK® (registered trademark) 1 and inoculated into the serum-free medium STK® (registered trademark) 2 and the synovial membrane or bone marrow mesenchymal stem cells separated in the 10% bovine serum-containing DMEM medium and inoculated into the serum-free medium STK® (registered trademark) 2 were cultured under conditions of 37° C. and 5% $CO_2$ for 10 days to 15 days.

Next, a rat of a cerebral infarction model was produced as an example of a central nervous disease (SPHPR-710-2 rat cerebral infarction model (Koizumi model)). A plug was inserted into the internal carotid artery of the rat so as to occlude the left middle cerebral artery. Thus, cerebral ischemia treatment was carried out. The plug was removed after 120 minutes from the occurrence of cerebral ischaemia so as to resume blood flow. Thus, a cerebrally infarcted model rat was produced.

Immediately after cerebral ischemia reperfusion, as Example (A), a group (A-G2) was produced to which synovial membrane-derived mesenchymal stem cells cultured with use of a serum-free medium had been administered through the caudal veins of cerebrally infarcted model rats at a rate of 0.8 mL/min over a period of 1 minute. As Comparative Example (B), a group (B-G2 or B-G3) was produced to which synovial membrane-derived or bone marrow-derived mesenchymal stem cells cultured with use of a 10% bovine serum-containing DMEM medium had been administered through the caudal veins of cerebrally infarcted model rats at a rate of 0.8 mL/min over a period of 1 minute, In this case, as negative controls (NC) for Example (A) and Comparative Example (B), a group (A-G1 or B-G1)

was produced to which SOLULACT® (registered trademark) infusion (TERUMO CORPORATION) containing no mesenchymal stem cells had been administered through the caudal veins of cerebrally infarcted model rats in the same manner as described above. Furthermore, as positive controls (PC) for Example (A) and Comparative Example (B), a group (A-G3 or B-G4) was produced to which 0.5 mg/kg of FK-506 (Tacrolimus, Astellas Pharma Inc.), which has been shown to reduce a cerebral infarct region, had been administered through the caudal veins of cerebrally infarcted model rats. Behavioral and histological evaluations were carried out with respect to the cerebral infarction model rat groups of Example (A) and Comparative Example (B) 1 day after the administration of the mesenchymal stem cells.

(Behavioral Evaluation)

Neurological symptoms of the cerebrally infarcted model rat groups of Example (A) and Comparative Example (B) were observed, and the behavioral evaluation was carried out. Each individual was scored in a range of 0 to 12 (a higher numerical value means a worse disease state) for the following 5 items: (1) fore limb paralysis, (2) hind limb paralysis, (3) rotational movement, (4) body side resistance, and (5) an ordinary state. Then, a sum of the scores for the 5 items was evaluated as a neurological symptom score.

Specifically, in the (1) fore limb paralysis, it was observed how the right fore limb of a rat lifted approximately 10 cm from a floor with its tail held was bent. A case where there was no difference in bending between the right and left fore limbs was measured as 0 point, a case where the right fore limb was slightly bent was measured as 1 point, a case where the right fore limb was bent approximately 90 degrees was measured as 2 points, and a case where it was impossible for the rat to move was measured as 3 points. Similarly, in the (2) hind limb paralysis, resilience of the hind limbs of the rat was observed in a case where the hind limbs were pulled while the rat was at rest. A case where there was no difference in muscular strength between the right and left hind limbs was measured as 0 point, a case where the right and left hind limbs were different in muscular strength was measured as 1 point, a case where a state of the hind limbs was made unnatural but was returned to the original state by a stimulus was measured as 2 points, and a case where the state of the hind limbs was made unnatural and the hind limbs did not respond to any stimulus was measured as 3 points. In the (3) rotational movement, a rotational movement of the rat with its tail held and its fore limbs placed on a surface of the floor was observed. A case where the rat moved forward was measured as 0 point, a case where the rat mainly moved forward but rotated clockwise was measured as 1 point, a case where the rat mainly rotated clockwise and also moved forward was measured as 2 points, and a case where the rat rotated clockwise only was measured as 3 points. In the (4) body side resistance, resistance of the rat was observed in a case where the right and left body sides of the rat were pushed one by one while the rat was at rest. A case where there was no difference between the right and left body sides was measured as 0 point, a case where the rat did not lose its balance but was vulnerable to a stimulus from the left was measured as point, a case where the stimulus from the left made it difficult for the rat to maintain the hind limbs was measured as 2 points, and a case where the rat toppled due to the stimulus from the left was measured as 3 points. In the (5) ordinary state, a body posture of the rat at rest was observed. A case where there was no difference from a normal animal was measured as 0 point, a case where the left limbs were protruding out of the body was measured as 1 point, a case where the rat was leaning to the right side was measured as 2 points, and a case where the rat was sharply leaning to the right side was measured as 3 points.

Figure 2:
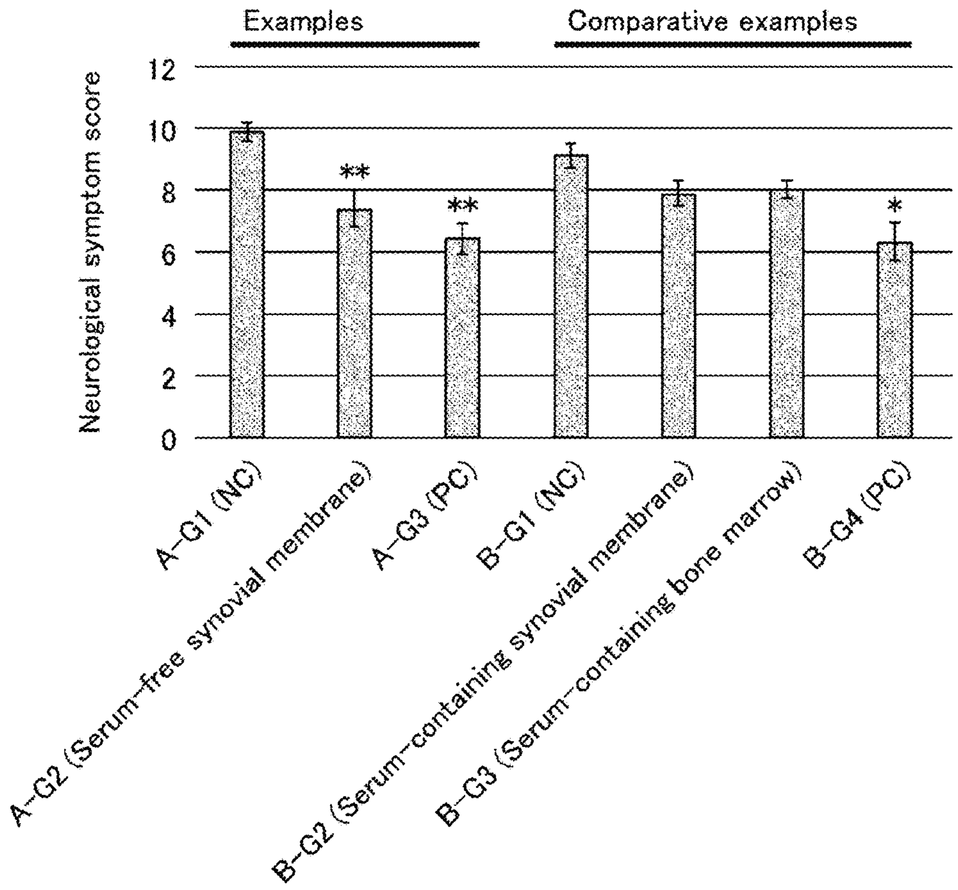
FIG. 2 is a diagram showing a result of measurement of a neurological symptom score in Example 1.

FIG. 2 shows a result of measurement of the neurological symptom score. Note that a Steel test was used to carry out statistical analyses of the neurological symptom score. In each of the analyses, it was assumed that a negative control was a control group and that a significant level was 5% on both sides. In the result of the measurement of FIG. 2, statistically significant differences are expressed as "*:P<0.05" and "**:P<0.01".

The result of the measurement of FIG. 2 was used to carry out the statistical analyses with respect to neurological symptoms in rats. As a result, the positive controls (A-G3 and B-G4) showed a more statistically significant (P<0.05) improvement in neurological symptom score than the negative controls (A-G1 and B-G1). This has shown that a condition of the neurological symptom score makes it possible to behaviorally evaluate recovery from cerebral infarction. The A-G2 to which synovial membrane-derived mesenchymal stem cells cultured in a serum-free medium had been administered showed a more statistically significant (P<0.01) improvement in neurological symptom score than the negative control. In contrast, the B-G2 or B-G3 to which synovial membrane-derived or bone marrow-derived mesenchymal stem cells cultured in a serum-containing medium had been administered showed no statistically significant difference from the negative control. Thus, the behavioral evaluation has shown that synovial membrane-derived mesenchymal stem cells cultured in a serum-free medium further improve a symptom of cerebral infarction than a case where mesenchymal stem cells cultured in a serum-containing medium are used.

(Histological Evaluation)

Subsequently, a volume of a cerebral infarct region of each of the cerebrally infarcted model rat groups of Example (A) and Comparative Example (B) was measured, and the histological evaluation was carried out. After the neurological symptoms were observed, the whole brain was removed, and a rat brain matrix was used to produce sections. The sections were each stained in a physiological saline solution containing 2% 2,3,5-triphenyltetrazolium chloride (TTC), and a scanner was used to capture an image for quantitative determination of the volume of the cerebral infarct region. OsiriX version 8.0.2 (Pixmeo SARL) was used to mark a TTC non-stained part in the image as the cerebral infarct region and measure an area of the TTC non-stained part. The measurement of the area was carried out with respect to the cerebral cortex and the basal ganglia. Respective total cerebral infarct regions ($mm^3$) of the cerebral cortex and the basal ganglia were calculated from the product of an area and a cross-sectional thickness (2 mm) of the cerebral infarct region in each cross section, and a sum of a volume of the total cerebral infarct region of the cerebral cortex and a volume of the total cerebral infarct region of the basal ganglia these volumes was regarded as a total cerebral infarct region volume.

Figure 3:
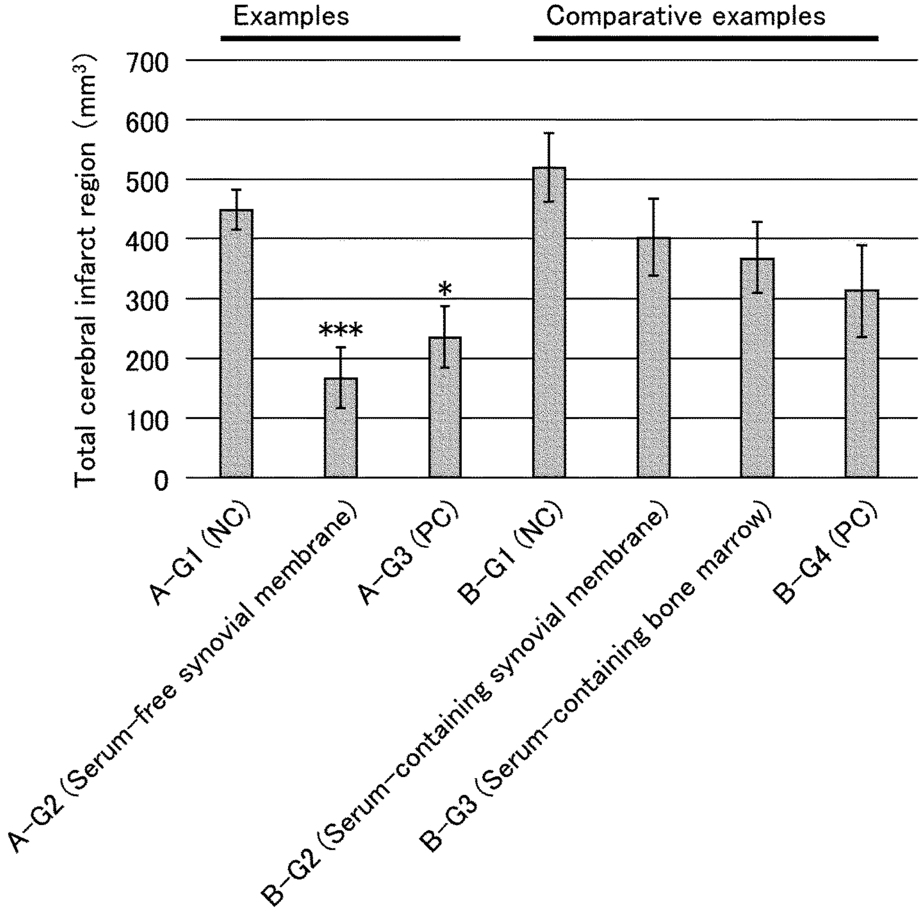
FIG. 3 is a diagram showing a result of measurement of an area of a total cerebral infarct region in Example 1.

FIG. 3 shows a result of measurement of an area of a total cerebral infarct region. Note that a Dunnett's test was used to carry out statistical analyses of the total cerebral infarct region. In each of the analyses, it was assumed that a negative control was a control group and that a significant level was 5% on both sides. In the result of the measurement of FIG. 3, statistically significant differences are expressed as "*:P<0.05" and "***:P<0.001".

The result of the measurement of FIG. 3 was used to carry out the statistical analyses of the total cerebral infarct region of rats. As a result, the A-G2 to which the synovial membrane-derived mesenchymal stem cells cultured in a serum-free medium had been administered showed a more statistically significant ($P<0.001$) improvement in neurological symptom score than the negative control. In addition, a smaller total cerebral infarct region was observed in the A-G2 also as compared with the positive control. In contrast, the B-G2 or B-G3 to which synovial membrane-derived or bone marrow-derived mesenchymal stem cells cultured in a serum-containing medium had been administered showed no statistically significant difference from the negative control. Thus, the histological evaluation also has shown that a case where synovial membrane-derived mesenchymal stem cells cultured in a serum-free medium are used further reduces the size of the cerebral infarct region than a case where mesenchymal stem cells cultured in a serum-containing medium are used.

A result of carrying out the behavioral and histological evaluations has shown that synovial membrane-derived mesenchymal stem cells cultured in a serum-free medium have an effect on a central nervous disease which effect cannot be achieved in a case where mesenchymal stem cells cultured in a serum-containing medium are used and which effect is remarkably high (i.e., so high as to be available for a clinical site).

Example 2

(Evaluation of Effectiveness of Synovial Membrane-Derived Mesenchymal Stem Cells Against Spinal Cord Injury)

Example 2 carried out a study on an improvement in sequelae of spinal cord injury due to transplantation of synovial membrane-derived mesenchymal stem cells cultured in a serum-free medium.

Figure 4:
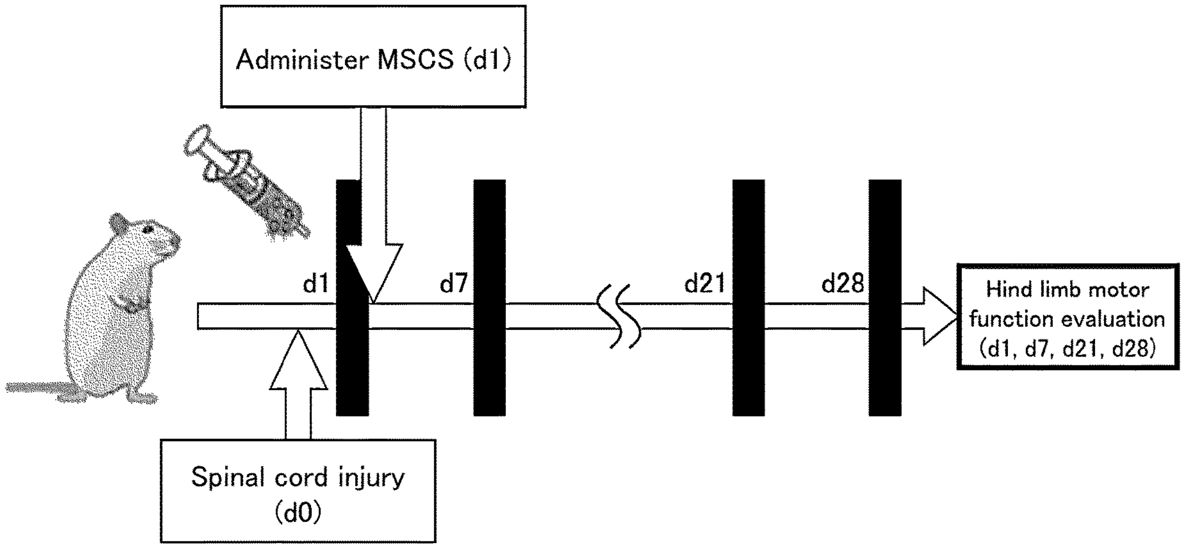
FIG. 4 is a diagram illustrating an outline of a procedure of an evaluation method in accordance with Example 2.

FIG. 4 illustrates an outline of a procedure of an evaluation method in accordance with Example 2. As illustrated in FIG. 4, Example 2 produced a spinal cord injured model rat, administered mesenchymal stem cells (MSCs) to the spinal cord injured model rat on the day after spinal cord injury, and carried out an evaluation of a hind limb motor function until the 4th week (28th day) after the spinal cord injury.

Experimental Example 2-1

Synovial membrane-derived mesenchymal stem cells were cultured as in the case of [Example 1]. Subsequently, spinal cord injured model rats obtained by a 50 mm weight-dropping method with use of a MASCIS impactor were produced as an example of a central nervous disease.

As Experimental Example 2-1, the following day after (24 hours after) spinal cord injury, a group (Cells, number of samples (n=3)) was produced to which synovial membrane-derived mesenchymal stem cells cultured with use of a serum-free medium had been gradually administered through the caudal veins of spinal cord injured model rats at a rate of 1 mL/min over a period of not less than 30 seconds. In this case, as a negative control, a group (Solvent, number of samples (n=3)) was produced to which SOLULACT® (registered trademark) infusion containing no mesenchymal stem cells had been administered through the caudal veins of spinal cord injured model rats in the same manner as described above. The following day, 7 days, 21 days, and 28 days after the spinal cord injury, a Basso-Beattie-Bresnahan (BBB) scale (see Basso et al., "A sensitive and reliable locomotor rating scale for open field testing in rats." J. Neurotrauma 1995; 12:1-21.) was used to carry out a hind limb motor function evaluation with respect to each of the spinal cord injured model rat groups.

(Hind Limb Motor Function Evaluation)

Figure 5:
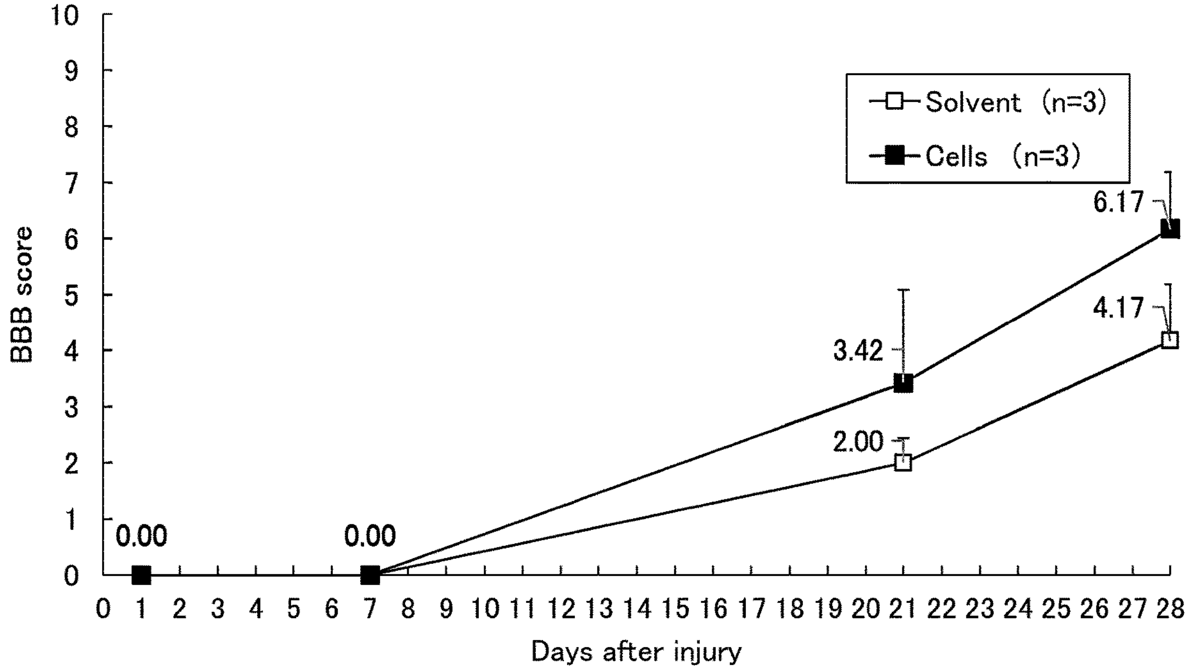
FIG. 5 is a diagram showing a result of measurement of BBB scores in Experimental Example 2-1 of Example 2.

FIG. 5 shows a measurement result obtained from the hind limb motor function evaluation. Note that statistical analysis of BBB scores was carried out by a Kruskal-Wallis test so as to study statistical significance. A significance level of less than 5% was intended to mean that there is a significant difference.

The result of the measurement of FIG. 5 made it possible to confirm a tendency of an improvement in BBB score in the Cells group to which synovial membrane-derived mesenchymal stem cells cultured in a serum-free medium had been administered, as compared with the Solvent group. The hind limb motor function evaluation has therefore suggested that synovial membrane-derived mesenchymal stem cells cultured in a serum-free medium improve a symptom of the spinal cord injury.

Experimental Example 2-2

Synovial membrane-derived mesenchymal stem cells were cultured as in the case of [Example 1]. Subsequently, rats different from the rats of Experimental Example 2-were used to produce spinal cord injured model rats obtained by a 50 mm weight-dropping method with use of a MASCIS impactor, as an example of a central nervous disease.

As Experimental Example 2-2, the following day after (24 hours after) spinal cord injury, a group (Cells, number of samples (n=6)) was produced to which synovial membrane-derived mesenchymal stem cells cultured with use of a serum-free medium had been gradually administered through the caudal veins of spinal cord injured model rats at a rate of 1 mL/min over a period of not less than 30 seconds. In this case, as a negative control, a group (Solvent, number of samples (n=6)) was produced to which SOLULACT (registered trademark) infusion containing no mesenchymal stem cells had been administered through the caudal veins of spinal cord injured model rats in the same manner as described above. The following day, 14 days, and 28 days after the spinal cord injury, a BBB scale was used to carry out a hind limb motor function evaluation with respect to each of the spinal cord injured model rat groups (the Cells group and the Solvent group).

(Hind Limb Motor Function Evaluation)

Figure 6:
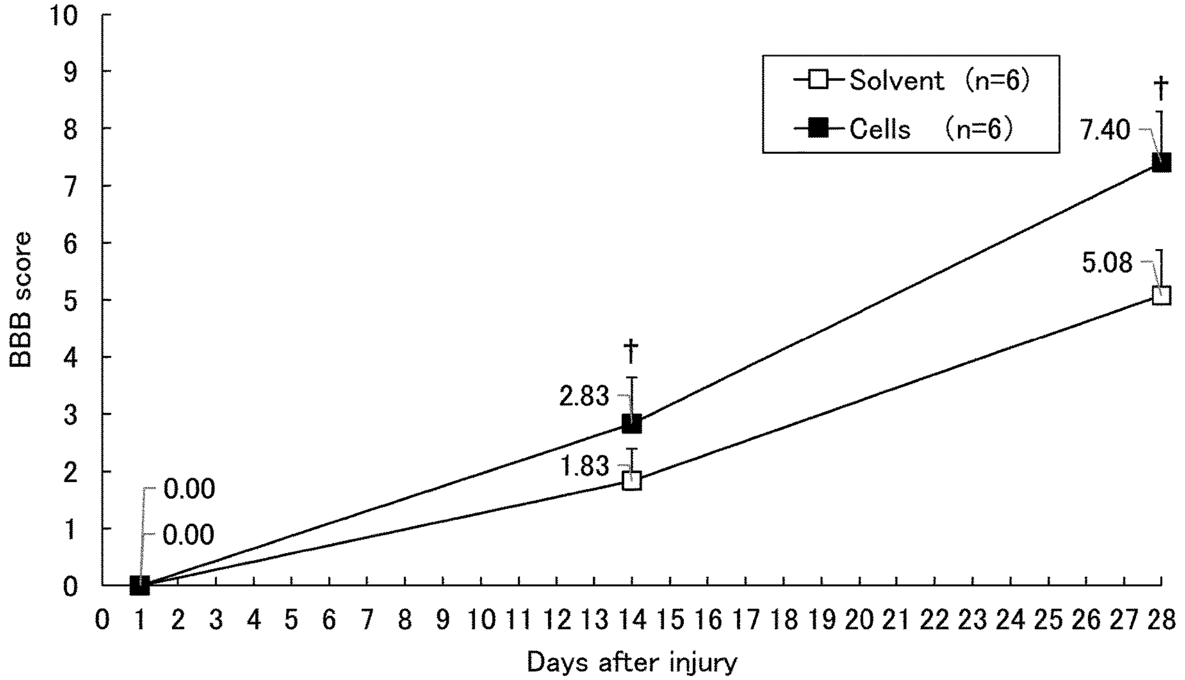
FIG. 6 is a diagram showing a result of measurement of BBB scores in Experimental Example 2-2 of Example 2.

FIG. 6 shows a measurement result obtained from the hind limb motor function evaluation. Note that statistical analysis of BBB scores was carried out by a t-test so as to study statistical significance. A case where a p-value is less than 0.10 was intended to mean that there is a tendency of significance. In the result of the measurement of FIG. 6, a tendency of statistical significance is expressed as "†:$P<0.10$".

The result of the measurement of FIG. 6 made it possible to confirm a tendency of a significant improvement in BBB score in the Cells group to which synovial membrane-derived mesenchymal stem cells cultured in a serum-free medium had been administered, as compared with the Solvent group serving as a negative control. The hind limb motor function evaluation has therefore also suggested that synovial membrane-derived mesenchymal stem cells cultured in a serum-free medium improve a symptom of the spinal cord injury.

INDUSTRIAL APPLICABILITY

The present invention makes it possible to provide a safer and highly useful therapeutic composition for treatment of a central nervous disease, the therapeutic composition containing mesenchymal stem cells. Thus, the present invention is suitably applicable to medicine in which mesenchymal stem cells are used for recovery and/or regeneration from central nervous diseases.

The invention claimed is:

1. A method for treating cerebral infarction, comprising the step of administering, to a target, synovial membrane-derived mesenchymal stem cells cultured in a serum-free medium, wherein the treating is amelioration of symptoms related to the cerebral infarction.

2. The method of claim 1, wherein the step of administering comprises an intravenous injection.

3. The method of claim 1, wherein the treating comprises administering from about $1\times10^4$ to $1\times10^{10}$ synovial membrane-derived mesenchymal stem cells per administration.

4. The method of claim 1, wherein the synovial membrane-derived mesenchymal stem cells are cryopreserved and thawed prior to the step of administering.

* * * * *